United States Patent [19]

Chiesi et al.

[11] Patent Number: 5,066,652
[45] Date of Patent: Nov. 19, 1991

[54] THIOMETHYL AND SULFINYLMETHYL DERIVATIVES HAVING GASTRIC ACID ANTISECTETORY ACTIVITY AND PHARMACEUTICAL COMPOSITIONS CONTAINING THEM

[75] Inventors: Paolo Chiesi; Vittorino Servadio; Roberta Razzetti, all of Parma, Italy

[73] Assignee: Chiesi Farmaceutici S.p.A., Parma, Italy

[21] Appl. No.: 494,864

[22] Filed: Mar. 14, 1990

Related U.S. Application Data

[63] Continuation of Ser. No. 223,160, Jul. 22, 1988, abandoned.

[30] Foreign Application Priority Data

Jul. 31, 1988 [IT] Italy ................... 21538 A/87

[51] Int. Cl.$^5$ .................. A61K 31/415; C07D 233/56
[52] U.S. Cl. ................. 514/235.8; 514/252; 514/326; 514/397; 514/398; 544/139; 544/370; 546/210; 548/336; 548/337
[58] Field of Search ............... 548/337, 336; 514/398, 514/225.8, 252, 326, 397; 544/139, 370; 546/210

[56] References Cited

U.S. PATENT DOCUMENTS 4,330,552 5/1982 Cherkofsky et al. ............. 514/398

FOREIGN PATENT DOCUMENTS 2038825 7/1980 United Kingdom .
2163747A 3/1986 United Kingdom .

OTHER PUBLICATIONS

Van Rossum, Arch. Intern. Pharmacodyn Ther., vol. 143, p. 305 (1963).
Goodman and Gilman's—The Pharmacological Basis of Therapeutics—7th Ed., MacMillan, N.Y., pp. 40-43 (1985).

*Primary Examiner*—Bernard Dentz
*Attorney, Agent, or Firm*—Walter H. Schneider

[57] ABSTRACT

Compounds of the formula

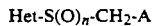

Het-S(O)$_n$-CH$_2$-A     (I)

wherein Het is a substituted imidazolyl, purinyl, thienoimidazolyl or imidazo-pyridyl group, n is 0 or 1, A is one of the following structures:

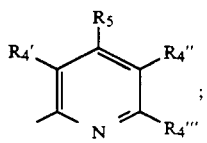

(II)

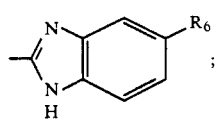

(III)

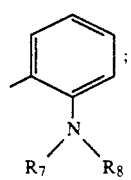

(IV)

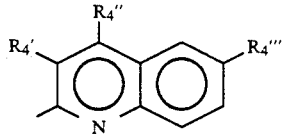

(V)

and their physiologically acceptable salts have antiulcer and gastric acid antisecretory activity.

9 Claims, No Drawings

THIOMETHYL AND SULFINYLMETHYL DERIVATIVES HAVING GASTRIC ACID ANTISECTETORY ACTIVITY AND PHARMACEUTICAL COMPOSITIONS CONTAINING THEM

This application is a continuation of application Ser. No. 223,160 filed July, 22, 1988 now abandoned.

The present invention relates to heterocyclic compounds and to physiologically acceptable salts thereof, having antiulcer and gastric acid antisecretory activities, to a process for the preparation thereof and to pharmaceutical compositions containing them.

The compounds of the invention have the following general formula:

Het-S(O)$_n$-CH$_2$-A   (I)

to which the following molecule classes belong, depending on Het meaning:

A. Imidazole derivatives of formula:

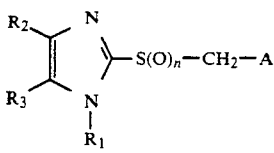

Ia wherein: R$_1$ is H, C$_1$-C$_4$ alkyl, benzyl or phenyl which can optionally be substituted by: C$_1$-C$_4$ alkyl, C$_1$-C$_4$ alkoxy, trifluoromethyl or halogens at any position; R$_2$ and R$_3$ are H or phenyl, with the proviso that when R$_1$=H, R$_2$ and R$_3$ are always phenyl; A is one of the following structures:

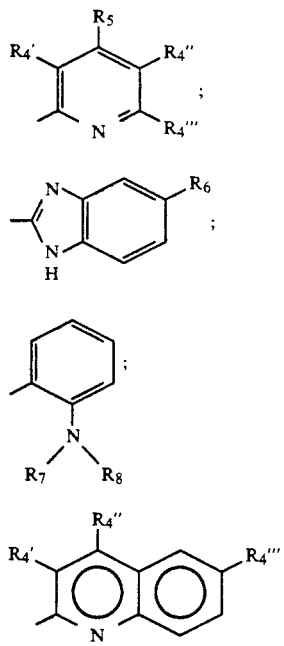

(II)

(III)

(IV)

(V)

wherein R$_4'$, R$_4''$ and R$_4'''$, which can be the same or different, are each hydrogen, C$_1$-C$_4$ alkyl or C$_1$-C$_4$ alkoxy with the proviso that when A=(II) they never are simultaneously H; R$_5$ is H or C$_1$-C$_4$ alkoxy; R$_6$ is H or benzoyl; R$_7$ and R$_8$, which can be the same or different, are each H, hydroxy-alkyl, C$_1$-C$_4$ alkyl possibly interrupted by heteroatoms such as O or N, and, together with the nitrogen atom to which they are bond, they can form a pyrrolidine, piperidine, piperazine or morpholine ring; n is 0 or 1.

B. Purine derivatives of formula:

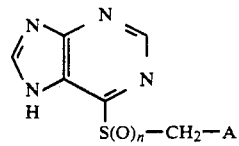

(Ib)

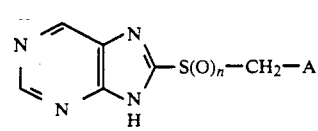

(Ib')

wherein A represents one of the structures (II), (IV) or (V) and n is 0 or 1.

C. Thieno-imidazole derivatives of formula:

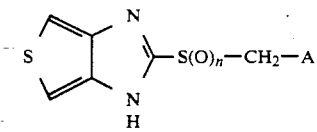

(Ic)

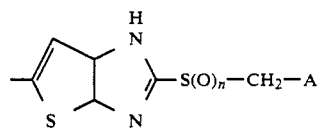

(Ic')

wherein A represents one of the structures (IV) or (V) and n is 0 or 1.

D. Imidazo-pyridine derivatives of formula:

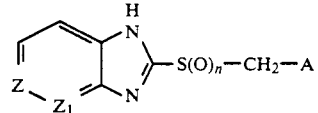

(Id)

wherein Z and Z$_1$, which are different from each other, are N or CH; A represents one of the groups (III), (IV) or (V), with the proviso that when A=(IV), R$_7$ and R$_8$ are always different from H or C$_1$-C$_4$ alkyl; n is 0 or 1.

A remarkable percentage (5-20%) of the european population is afflicted, at some point of its existence, with gastroduodenal ulcer.

The illness'medical treatment, principally based till now on reduction or neutralization of the intraduodenal and intragastric acidity, has marked considerable progress in the last 10 years.

The arrival of the antagonists of H$_2$ histamine receptors, cimetidine and ranitidine, has caused a true revolution in this therapeutic sector, thus stimulating the research for new drugs of increased power and effectiveness.

As a result, a new pharmacological class of antisecretory drugs has been located, the so-called inhibitors of the protonic pump, the more representative being omeprazole, a substituted derivative of benzimidazole endowed with a lasting and powerful inhibiting activity of gastric acid secretion. The search for drugs of an ever increasing power of inhibition of the acid secretion has however created problems. In fact, deep and prolonged inhibition of the acid secretion can cause morphologic alterations in the mucous membrane.

A high incidence of carcinomas at the bottom of the stomach has been observed in animals treated over a long period with either omeprazole or powerful antagonists of $H_2$ receptors, so much so that development of some of these products has been temporarily or definitively shelved.

Moreover, among the patients treated with very powerful anti-secretory agents, a considerable relapse frequency, direct consequence of the type of therapy, has been noted.

Novel therapeutic prospects in the treatment of gastroduodenal ulcer were opened recently by cytoprotective drugs which seem to act by strengthening the defense of the mucous barrier, by means of a process independent from the inhibition of acid secretion.

The mucous membrane's protective drugs have rekindled the interest in the study of the ulcerative mechanism giving new credit to the hypothesis that it derives from a diminished resistance to the acid-peptic activity rather than to an increase of the secretory activity.

The problem of therapy of ulcer therefore remains unresolved. A rational approach seems to be control of acid secretion rather than a too strong inhibition, on one side, and improved resistance of the mucous membrane to the attacks of the acid and of the other damaging agents, on the other.

Future strategy in the therapy of peptic ulcer can lie therefore with the use of inhibitors of acid secretion associating a protective action of the mucous membrane.

In this perspective, various classes of molecules have been prepared in the aim to value their potentiality of use in the treatment of gastroduodenal ulcer.

As previously said, considerable interest was caused recently by a new class of inhibitors of gastric acidity consisting in benzimidazole derivatives, of which the omeprazole seems to be at this moment the more powerful.

Omeprazole, described in European Patent No. 5129, can be considered the final result of a series of studies on analogous structures object of previous patents Nos. DE 2504252 and DE 2548340.

Heterocyclic thioalkyl and thiosulfinyl derivatives of various structures, having antisecretory activity, are also disclosed in EP-A-74.341, GB Patent No. 2.134.523, GB Patent No. 2.038.825, GB Patent No. 2.161.160 and, more recently, in EP-A-201.094. Nevertheless said compounds, on the basis of the activity results reported in the above-mentioned patents, seem to show no remarkable advantages in comparison with omeprazole.

Thus, the present inventors have prepared different series of thioalkyl and thiosulfinyl-derivatives belonging to various molecular classes, of general formula:

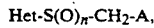

in order to verify the influence on the compound activity of both Het heterocyclic ring and A aromatic groups and of selected substitutions on said rings.

The process for the preparation of derivatives of formula (I) in which n=0 consists in reacting a compound of formula Het-SH (VI), wherein Het has the above mentioned meanings, with a compound of formula:

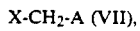

wherein A has one of the above mentioned meanings and X is a leaving group, preferably an halogen atom.

The reaction is conveniently carried out in the presence of a solvent or a mixture of solvents which are inert under the reaction conditions, generally in the presence of a base. Suitable bases are, in particular, inorganic bases, such as sodium or potassium hydroxides, or organic bases, such as triethylamine or tertiary amines.

Alternatively, the reaction can be carried out in a biphasic system, in the presence of a catalyst.

Particularly suitable solvents or solvent mixtures are alcohols, such as methanol or ethanol, mixtures of alcohols and water, preferably ethanol-water; ethers, such as tetrahydrofuran or dioxane; halogenated hydrocarbons, such as methylene chloride or chloroform; amides, such as formamide or dimethylformamide.

The reaction temperature usually ranges from room temperature to the boiling temperature of the reaction mixture.

A particularly convenient preparation method consists in transforming a compound of formula (VI) into the corresponding alkali salt using, for example, a sodium hydroxide solution, subsequently adding to the solution a compound (VII), in which X preferably represents a halogen such as chlorine, bromine or iodine. Corresponding compounds of formula (I) in which n is 1 are obtained by subsequent oxidation of the sulfur atom to sulfinyl group (S→O).

The used oxidation agents are those generally employed in the trasformation of S into S→O, which are selected from: peracids, particularly m-chloroperbenzoic acid, p-nitroperbenzoic acid; hydrogen peroxide, peresters, sodium metaperiodate, selenium dioxide, manganese dioxide, etc.

Oxidation is conveniently carried out in an organic solvent inert in the reaction conditions, such as ethanol, dimethylformamide, ethyl ether, a halogenated hydrocarbon, preferably methylene chloride, chloroform, dichloroethane, or an aromatic hydrocarbon, such as benzene and similar.

The oxidation agent is generally used in excess to the compound to be oxidized. Oxidation is conveniently effected at room temperature or at a lower temperature from −10° C. to 0° C.

Compounds of general formula I are obtained as the free bases or as the acids, depending on the reaction conditions.

Free bases can be in their turn transformed into the corresponding pharmaceutically acceptable salts, by addition of therapeutically compatible organic or inorganic acids, such as hydrochloric, hydrobromic, phosphoric, sulfuric, citric, acetic, succinic, maleic, methanesulfonic, p-toluenesulfonic acids, and the like.

Compounds of formula (I) in which n=1, can be in form of optical isomers or racemates, all these forms being comprised in the present invention.

Reaction intermediates of formula (VI) and (VII) are generally commercially available or they can be prepared according to procedures known in literature. If not, the preparation thereof is reported in the examples.

The invention is described in more detail in the following non-limiting examples.

EXAMPLE 1

1-methyl-2-[2'-(3',5'-dimethyl-4'-methoxypyridyl)methylthio]imidazole.2HCl (VIII)

17.00 g (0.076 mole) of 2-chloromethyl-3,5-dimethyl-4-methoxypiridine hydrochloride was added to a solution of 2-mercapto-1-methylimidazole (8.74 g–0.076 mole) in sodium hydroxide (6.12 g–0.150 mole) and the mixture was refluxed for about 2.5 hours.

The reaction mixture was cooled, filtered and evaporated. The residue was taken up in dichloromethane and washed with 100 ml portions first of 0.5N sodium hydroxide, then of water; the organic solution was decolorized with animal charcoal, dried over sodium sulfate and evaporated. The oily residue, about 20 g (100% yield), was precipitated and crystallized as the hydrochloride by treating its ethanol solution with ether saturated with hydrochloric acid.

Yield 92%; $C_{13}H_{19}Cl_2N_3OS$; M.W. 336.28; m.p. 157°–158° C.

By an analogous process, using 2-mercapto-1-methylimidazole and the corresponding chloromethyl derivatives as starting materials, the following compounds were obtained:

1-methyl-2-(2'-benzimidazolylmethylthio)imidazole.2HCl (IX). $C_{12}H_{14}Cl_2N_4S$; M.W. 317.24; m.p. 235°–238° C.;

1-methyl-2-[2'-(5'-benzoyl)-benzimidazolylmethylthio]imidazole. $2H_3PO_4$ (X). $C_{19}H_{21}N_4P_2O_9S$; M.W. 543.40; m.p. 156°–158° C.;

1-methyl-2-[2'-(N,N-dimethylanilyl)methylthio]imidazole. 2HCl (XI).

$C_{13}H_{19}Cl_2N_3S$; M.W. 320.28; m.p. 172°–177° C.;

1-methyl-2-(2'-quinolylmethylthio)imidazole.2HCl (XII). $C_{14}H_{15}Cl_2N_3S$; M.W. 328.26; m.p. 178°–182 ° C.;

1-methyl-2-[2'-(4'-methoxypyridyl)methylthio]imidazole. $2CH_3SO_3H$ (XIII). $C_{13}H_{21}N_3O_7S_3$; 427.51; m.p. 134°–137° C.

EXAMPLE 2

1-methyl-2-[2'-(3',5'-dimethyl-4'-methoxy)pyridylmethylsulfinyl]imidazole (XIV)

9.0 g (0.034 mole) of the thioether obtained in example 1 was dissolved in 40 ml of chloroform; the mixture was cooled in ice-salt bath to −10° C. 7.2 (0.035 mole) of 85% m-chloroperbenzoic acid dissolved in about 30 ml of chloroform was added dropwise, under stirring, keeping temperature below −5° C.; thereafter temperature was raised to 5° C., under stirring. The reaction mixture was diluted with chloroform and washed with two 60 ml portions, first of 0.5N NaOH, then of water, to neutral. Chloroform solution was dried over sodium sulfate, filtered and evaporated under reduced pressure to obtain two lots of a brown-yellow oil of about 5 g each, which were purified by flash chromatography. By evaporation at 50° C. under reduced pressure 6.3 g of the compound was obtained.

Yield 66%; $C_{13}H_{17}N_3O_2S$; M.W. 279.36; m.p. 93°–95° C.

By the same process, using the corresponding thioether as the starting compound, by reaction with m-chloroperbenzoic acid, the following sulfinyl derivatives were obtained:

1-methyl-2-[2'-(5'-benzoyl)benzimidazolylmethylsulfinyl]imidazole (XV). $C_{19}H_{14}N_4O_2S$; M.W. 364.43; m.p. 116°–120° C.;

1-methyl-2-[2'-(4'-methoxypyridyl)methylsulfinyl]imidazole (XVI). $C_{13}H_{21}N_3O_8S_3$; M.W. 443.51; m.p. 155°–157° C.

Analogously, using dichloromethane as the solvent and directly recovering the product from the reaction mixture after washing with ether and drying, 1-methyl-2-[2'-benzimidazolylmethylsulfinyl)imidazole (XVII) was obtained. $C_{12}H_{12}N_4OS$; M.W. 260.32; m.p. 164° C. (dec.).

By a process similar to that described for compound (XVII), but recrystallizing from acetonitrile, 1-methyl-2-(2'-quinolylmethylsulfinyl)imidazole (XVIII) was obtained.

$C_{14}H_{13}N_3OS$; M.W. 271.34; m.p. 123°–124° C.

EXAMPLE 3

1-(3'-fluorophenyl)-2-[2'-(N,N-dimethylanilyl)methylthio]imidazole.2HCl (XIX)

To a solution of 7 g (0.175 mole) of sodium hydroxide in 8 ml of water and 115 ml of absolute ethanol, 10 g (0.043 mole) of 1-(3'-fluorophenyl)-2-mercaptoimidazole hydrochloride and then 9 g (0.044 mole) of N,N-dimethylaminobenzyl chloride was added under stirring, keeping temperature at about room temperature by means of a cold water bath.

Stirring was maintained for 3 hours at room temperature and for 1.5 hours at 35°–40° C. The final mixture was filtered and the solution was evaporated under reduced pressure at a temperature below 40° C. to obtain an oil. The oil was taken up in dichloromethane and the organic solution was extracted with three 100 ml portions of 0.5N sodium hydroxide, finally with a 100 ml portion of water. The organic solution was dried over sodium sulfate, filtered and evaporated to obtain an oil which was further purified by flash chromatography using a 50:50 ethyl acetate/n-hexane mixture as the eluent. The selected fractions were evaporated, the resulting oil was dissolved in 50 ml ethyl ether and added with ether saturated with hydrochloric acid to markedly acid pH. The ether solution was evaporated to obtain a white very hygroscopic solid.

Yield 67%; $C_{18}H_{20}Cl_2FN_3S$; M.W. 400.34; m.p. 120° C. (dec.);

By a process analogous to that of example 3, using the respective 2-mercaptoimidazole derivatives as starting materials and the corresponding chloromethyl derivatives, the following compounds were prepared:

1-(3'-fluorophenyl)-2-[2'-(3'-methyl-4'-methoxypyridyl)methylthio]imidazole (XX); $C_{17}H_{16}FN_3OS$; M.W. 329; m.p. 86°–89° C.;

1-(3'-fluorophenyl)-2-[2'-(benzimidazolyl)methylthio]imidazole.2HCl (XXI); $C_{17}H_{14}Cl_2FN_4S$; M.W. 397.01; m.p. 240° C. (dec.);

1-phenyl-2-[2'-(benzimidazolyl)methylthio]imidazole.2HCl (XXII); $C_{17}H_{17}Cl_2N_4S$; M.W. 397.01; m.p. 135°–140° C.;

1-phenyl-2-[2'-(3'-methyl-4'-methoxypyridyl)methylthio]imidazole (XXIII); $C_{17}H_{17}N_3OS$; M.W. 311.4; m.p. 76°–78° C.;

1-(4'-fluorophenyl)-2-[2'-benzimidazolyl)methylthio]imidazole (XXIV); $C_{17}H_{13}FN_3S$; M.W. 324.37; m.p. 147°–151° C.

1-(4'-fluorophenyl)-2-[2'-(3'-methyl-4'-methoxypyridyl)methylthio]imidazole (XXV); $C_{17}H_{16}FN_3OS$; M.W. 329.4; m.p. 71°–73° C.;

4,5-diphenyl-2-[2'-(3',5'-dimethyl-4'-methoxypyridyl)methylthio]imidazole (XXVI); $C_{24}H_{23}N_3OS$; M.W. 401.52; m.p. 130°–134° C.;

4,5-diphenyl-2-[2'-(N,N-dimethylanilyl)methylthio]imidazole (XXVII); $C_{24}H_{23}N_3S$; M.W. 385.53; m.p. 155°–157° C.;

1-phenyl-2-[2'-(N,N-dimethylanilyl)methylthio]imidazole. 2HCl (XXVIII); $C_{18}H_{21}Cl_2N_3S$; M.W. 382.35; m.p. 125° C. dec.

1-(4'-methoxyphenyl)-2-[2'-(N,N-dimethylanilyl)methylthio]imidazole.2HCl (XXIX); $C_{19}H_{23}Cl_2N_3OS$; M.W. 412.3; m.p. 182°–186° C.;

1-(4'-fluorophenyl)-2-[2'-(N,N-dimethylanilylmethylthio]imidazole (XXX); $C_{18}H_{20}Cl_2FN_3S$; M.W. 400.36; m.p. 179°–183° C.;

1-(2'-clorophenyl)-2-[2'-(N,N-dimethylanilyl)methylthio]imidazole (XXXI); $C_{18}H_{18}ClN_3S$; M.W. 343.9; m.p. 75°–77° C.;

1-(2'-fluorophenyl)-2-[2'-(N,N-dimethylanilyl)methylthio]imidazole (XXXII); $C_{18}H_{18}FN_3S$; M.W. 327.42; m.p. 59°–62° C.;

1-(2'-methoxyphenyl)-2-[2'-(N,N-dimethylanilyl)methylthio]imidazole (XXXIII); $C_{19}H_{21}N_3OS$; M.W. 349; m.p. 64°–68° C.;

1-(4'-chlorophenyl)-2-[2'-(N,N-dimethylanilyl)methylthio]imidazole. 2HCl (XXXIV); $C_{18}H_{20}Cl_3N_3S$; M.W. 416.87; m.p. 179°–181° C.;

1-(2'-trifluoromethylphenyl)-2-[2'-(N,N-dimethylanilyl)methylthio]imidazole. 2HCl (XXXV); $C_{19}H_{20}Cl_2F_3N_3S$; M.W. 450.12; m.p. 160°–170° C.;

1-phenyl-2-[2'-(quinolyl)methylthio]imidazole (XXXVI); $C_{19}H_{15}N_3S$; M.W. 317.41; m.p. 89°–91° C.

EXAMPLE 4

1-(3'-fluorophenyl)-2-[2'-(3'-methyl-4'-methoxypyridyl)methylsulphinyl]imidazole (XXXVII)

4.5 g (0.0136 mole) of the thioether obtained as in example 3, dissolved in 100 ml of dichloromethane and kept to a temperature from −5° to −10° C. were added dropwise with a solution of 2.83 g (0.139 mole) of m-chloroperbenzoic acid dissolved in about 15 ml of dichloromethane, stirring for about 45 minutes. The reaction mixture was diluted with dichloromethane and washed with 3×100 ml portions of 0.5N sodium hydroxide and dried over sodium sulfate. The solution was evaporated and the obtained oil was purified by flash chromatography. The selected fractions were evaporated and the product was treated with some dichloromethane, from which a white compound solidified which was recovered by filtration and drying at room temperature.

Yield: 79.8%; $C_{17}H_{16}FN_3O_2S$; M.W. 345.4; m.p. 139°–143° C.

By a process similar to that described in example 4, starting from 4,5-diphenyl-2-[2'-(3',5-dimethyl-4'-methoxypyridyl)methylthio] imidazole, the following compounds were obtained:

4,5-diphenyl-2-[2'-(3',5'-dimethyl-4'-methoxypyridyl)methylsulfinyl]imidazole (XXXVIII); $C_{24}H_{23}N_3O_2S$; M.W. 417.53; m.p. 163°–165° C.;

1-(4'-fluorophenyl)-2-[2'-(benzimidazolyl)methylsulfinyl]-imidazole (XXXIX); $C_{17}H_{13}FN_4OS$; M.W. 340.38; m.p. 153°–156° C. dec.;

1-(3'-fluorophenyl)-2-[2'-(benzimidazolyl)methylsulfinyl]imidazole (XL); $C_{17}H_{13}FN_4OS$; M.W. 340.38; m.p. 171° C. dec.;

1-(2'-fluorophenyl)-2-[2'-(N,N-dimethylanilyl)methylsulfinyl]imidazole (XLI); $C_{18}H_{18}FN_3OS$; M.W. 343.42; m.p. 137°–139° C.;

1-phenyl-2-[2'-(quinolyl)methylsulphinyl]imidazole (XLII); $C_{19}H_{15}N_3OS$; M.W. 333.41; m.p. 128°–130° C.

EXAMPLE 5

6-[2'-(6'-methyl-3'-methoxypiridyl)methylthiopurine (XLIII)

17.02 g (0.1 mole) of 6-mercaptopurine monohydrate were added to a solution of 8.15 g (0.2 mole) of 98% sodium hydroxide in 30 ml of water and 320 ml of absolute ethanol, stirring and heating to 60° C. to complete dissolution. Then 20.81 g (0.1 mole) of 2-chloromethyl-6-methyl-3-methoxypyridine was added to the mixture under strong stirring and the mixture was refluxed for about 3 hours, then it was left to cool; the inorganic precipitate was filtered and the filtrate was concentrated to about 100 ml.

The concentrate was kept at low temperature until crystallization of the product. The mixture was filtered and the solid was washed with absolute ethanol, then water, finally filtered and dried at 90° C. under reduced pressure, to yield 25.5 g of the compound.

Yield 88.8%; $C_{13}H_{13}N_5OS$; M.W. 287.33; m.p. 189°–188° C.;

By a process similar to that of Example 5, using an appropriate mercaptopurine and the corresponding chloromethyl derivatives, the following compounds were obtained:

6-[2'-(3'methyl-4'-methoxypyridyl)methylthio]purine (XLIV); $C_{13}H_{13}N_5OS$; M.W. 287.33; m.p. 210°–220° C.;

8-[2'-(N,N-dimethylanilyl)methylthio]purine (XLV); $C_{14}H_{15}N_5S$; m.p. 164°–169° C.

EXAMPLE 6

6-[2'-(6'-methyl-3'-methoxypyridyl)methylsulfinyl]purine (XLVI)

10.0 g ,(0.035 mole) of the thioether, prepared as in example 5, was dissolved in 180 ml of a 15:10 ethanol/dichloromethane mixture . 7.9 g (0.039 mole) of 85% m-chloroperbenzoic acid was added to the starting solution in anhydrous medium, at −5° C. under strong stirring, leaving the reaction mixture to react in the cool for 1 hour. The solution was warmed to room temperature and evaporated at 45° C. under reduced pressure. The crude residue was crystallized from cool ethanol, to obtain a white solid.

Yield 62%; $C_{13}H_{13}N_5O_2S$; M.W. 303.33; m.p. 163°–165° C.

EXAMPLE 7

2-(2'-[1'-(4-morpholinyl)phenyl]methylthio)imidazo-[4,5-b]-pyridine (XLVII)

6.0 g (0.04 mole) of 2-mercaptoimidazo-[4,5-b]-pyridine were dissolved in 156 ml of a solution of 3.3 g (0.08 mole) of sodium hydride in a 25:1 ethanol/water mixture. Then 10 g (0.04 mole) of 2-chloromethyl-1-(4-morpholinyl)benzene hydrochloride were added and the mixture was reacted for 2 hours at room temperature; thereafter it was cooled to about 5°–8° C. and filtered.

The resulting solid was washed with water and methanol and the product was dried at 40° C. under reduced pressure.

Yield 65%; $C_{17}H_{18}N_4OS$; M.W. 326.43; m.p. 199°–203° C.

By a similar process, using the same 2-mercapto derivative and the corresponding chloromethyl derivatives as starting compounds, the following componds were obtained:

2-(2'-benzimidazolylmethylthio)imidazo-[4,5-b]-pyridine (XLVIII), isolated in form of monohydrate dihydrochloride; $C_{14}H_{15}Cl_2N_5OS$; M.W. 372.27; m.p. 249°–252° C.;

2-(2'-quinolylmethylthio)imidazo-[4,5-b]-pyridine (XLIX), isolated in form of dihydrochloride; $C_{16}H_{14}Cl_2N_4S$; M.W. 365.2; m.p. 183°–187° C.

Again by the similar process, using 2-mercaptoimidazo-[4,5-c]-pyridine and 2-chloromethyl-1,1-dimethyl)aniline as starting products, 2-[2'-(N,N-dimethylanilyl)methylthio]imidazo-[4,5-c]-pyridine (L) was obtained: $C_{15}H_{16}N_4S$; M.W. 284.38; m.p. 180°–183° C.

EXAMPLE 8

2-(2'-quinolylmethylsulfinyl)imidazo-[4,5-b]-pyridine (LI)

9 g (0.035 mole) of the thioether prepared according to example 7 was dissolved in 350 ml of a 10:70 ethanol/dichloromethane mixture. 7.9 g (0.039 mole) of 85% m-chloroperbenzoic acid was added to the starting solution in anhydrous medium, at −10° C., under strong stirring and the mixture was left to react in the cool for 1 hour, then it was warmed to room temperature and filtered. The solid was taken up in ethanol and dried in oven at 30° C.

Yield 91%; $C_{16}H_{12}N_4OS$; m.p. 185°–190° C.

EXAMPLE 9

2-[2'-(N,N-dimethylanilyl)methylthio)thieno-[3,4-d]-imidazole (LII)

5.0 g (0.032 mole) of 2-mercaptothieno-[3,4--d]-imidazole was added to a solution of 2.68 g (0.065 mole) of 98% sodium hydroxide (0.0657 mole) and of an ethanol/water mixture (respectively 150 ml and 10 ml), under stirring, till complete dissolution. Then 6.8 g (0.0328 mole) of 2-chloromethyl-N,N-dimethylaniline hydrochloride dissolved in 50 ml of absolute ethanol was added and the mixture was reacted for about 2 hours at room temperature. After filtration, the solution was evaporated at 40° C. under reduced pressure. The residue was taken up in 200 ml of dichloromethane, washed with 50 ml on a 0.5N sodium hydroxide solution, finally with 150 ml of water. The organic phase was treated with actived carbon, silica, and after filtration, the obtained product was separated by chromatography.

Yield 51%; $C_{14}H_{15}N_3S_2$; m.p. 137°–143° C.

EXAMPLE 10

5-benzoyl-2-chloromethyl-benzimidazole (LIII)

3,4-diaminobenzophenone (53 g, 0.25 mole) chloroacetic acid (47.2 g, 0.50 mole) and 4N HCl (250 ml, 1 mole) were refluxed for 3 hours. The mixture was left to stand during night and the solid was filtered, then vigorously crushed in a water (500 ml) and $CH_2Cl_2$ (800 ml) mixture.

6N $NH_4OH$ was slowly added to the emulsion, under strong stirring, till neutral, at about 10° C. The phases were separated. Organic phase was subsequently dried over sodium sulfate, treated with active carbon and dried again under reduced pressure.

Yield about 60%; $C_{15}H_{11}ClN_2O$; M.W. 270.72.

The compound was used as an intermediate for the preparation of compounds of formula (I) in which A is a (III) group and $R_6$ is benzoyl, e.g. compounds X and XV.

The structure of the final compounds was confirmed by the elemental analysis and by the respective NMR and IR spectra.

The exemplified compounds are summarized in Tables 1 and 2.

TABLE 1

N-substituted imidazole derivatives.

| Comp. No | $R_1$ | $R_2$ | $R_3$ | n | A | CODE (CHF) | PF °C. |
|---|---|---|---|---|---|---|---|
| VIII | Me | H | H | 0 | 2-(3,5-Me-4-MeO)Py | 1340 | 157–158 |
| IX | Me | H | H | 0 | 2-benzimidazolyl.2HCl | 1316 | 235–238 |
| X | Me | H | H | 0 | 2-(5-PhCO)benzimidazolyl $2H_3PO_4$ | 1376 | 156–158 |
| XI | Me | H | H | 0 | 2-(N,N-Me)anilyl.2HCl | 1472 | 172–176 |
| XII | Me | H | H | 0 | 2-quinolyl.2HCl | 1240 | 178–182 |
| XIII | Me | H | H | 0 | 2-(4-MeO)Py.dimethanesulfonate | 1374 | 134–137 |
| XIV | Me | H | H | 1 | 2-(3,5-Me-4-MeO)Py | 1338 | 93–95 |
| XV | Me | H | H | 1 | 2-(5-PhCo)benzimidazolyl | 1360 | 116–120 |
| XVI | Me | H | H | 1 | 2-(4-MeO)Py.dimethanesulfonate | 1979 | 155–159 |
| XVII | Me | H | H | 1 | 2-benzimidazolyl | 1337 | 164 dec. |
| XVIII | Me | H | H | 1 | 2-quinolyl | 1263 | 123–124 |
| XIX | m-FPh | H | H | 0 | 2-(N,N-Me)anilyl.2HCl | 1477 | 120 dec. |
| XX | m-FPh | H | H | 0 | 2-(3-Me-4-MeO)Py | 1451 | 86–89 |
| XXI | m-FPh | H | H | 0 | 2-benzimidazolyl.2HCl | 1454 | 240 dec. |
| XXII | Ph | H | H | 0 | 2-benzimidazolyl | 1446 | 135–140 |
| XXIII | Ph | H | H | 0 | 2-(3-Me-4-MeO)Py | 1449 | 76–78 |
| XXIV | p-FPh | H | H | 0 | 2-benzimidazolyl | 1450 | 147–151 |
| XXV | p-FPh | H | H | 0 | 2-(3-Me-4-MeO)Py | 1452 | 71–73 |
| XXVI | H | Ph | Ph | 0 | 2-(3,5-Me-4-MeO)Py | 1444 | 130–134 |
| XXVII | H | Ph | Ph | 0 | 2-(N,N-Me)anilyl | 1471 | 155–157 |
| XXVIII | Ph | H | H | 0 | 2-(N,N-Me)anilyl.2HCl | 1700 | 125 dec |
| XXIX | p-MeOPh | H | H | 0 | 2-(N,N-Me)anilyl.2HCl | 1740 | 182–186 |
| XXX | p-FPh | H | H | 0 | 2-(N,N-Me)anilyl.2HCl | 1757 | 179–183 |
| XXXI | o-ClPh | H | H | 0 | 2-(N,N-Me)anilyl | 1759 | 75–77 |
| XXXII | o-FPh | H | H | 0 | 2-(N,N-Me)anilyl | 1760 | 59–62 |
| XXXIII | o-MeOPh | H | H | 0 | 2-(N,N-Me)anilyl | 1765 | 64–68 |
| XXXIV | p-ClPh | H | H | 0 | 2-(N,N-Me)anilyl.2HCl | 1766 | 179–181 |

TABLE 1-continued

N-substituted imidazole derivatives.

| Comp. No | R₁ | R₂ | R₃ | n | A | CODE (CHF) | PF °C. |
|---|---|---|---|---|---|---|---|
| XXXV | o-CF₃Ph | H | H | 0 | 2-(N,N-Me)anilyl.2HCl | 1768 | 160–170 |
| XXXVI | Ph | H | H | 0 | 2-quinolyl | 1769 | 89–91 |
| XXXVII | m-FPh | H | H | 1 | 2-(3-Me-4-MeO)Py | 1458 | 139–143 |
| XXXVIII | H | Ph | Ph | 1 | 2-(3,5-Me-4-MeO)Py | 1469 | 163–165 |
| XXXIX | p-FPh | H | H | 1 | 2-benzimidazolyl | 1724 | 153–156 dec |
| XL | m-FPh | H | H | 1 | 2-benzimidazolyl | 1729 | 171 dec |
| XLI | o-FPh | H | H | 1 | 2-(N,N-Me)anilyl | 1764 | 137–139 |
| XLII | Ph | H | H | 1 | 2-quinolyl | | 128–130 |

TABLE 2

Imidazo-purine derivatives.
Purine derivative
Thieno-imidazo derivatives of the general formula:

$$\text{Het}-\overset{(O)_n}{S}-CH_2-A$$

| Comp. No | n | Het | A | CHF | PF °C. |
|---|---|---|---|---|---|
| XLIII | 0 | 6-purinyl | 2-(3-MeO-6-Me)Py | 1272 | 186–188 |
| XLIV | 0 | 6-purinyl | 2-(4-MeO-3-Me)Py | 1713 | 210–220 |
| XLV | 0 | 8-purinyl | 2-(n,N-Me)anilyl | 1758 | 164–169 |
| XLVI | 1 | 6-purinyl | 2-(3-MeO-6-Me)Py | 1728 | 163–165 |
| XLVII | 0 | 1H-imidazo-[4,5-b]-pyridin-2-yl | 2[1(4-morfolinyl)phenyl | 1763 | 199–203 |
| XLVIII | 0 | 1H-imidazo-[4,5-b]-pyridin-2-yl | 2-benzimidazolyl | 1341 | 249–252 |
| LIX | 0 | 1H-imidazo-[4,5-b]-pyridin-2-yl | 2-quinolyl.2HCl | 1749 | 183–187 |
| L | 0 | 1H-imidazo-[4,5-c]-pyridin-2-yl | 2-(N,N-Me)anilyl | 1754 | 180–183 |
| LI | 1 | 1H-imidazo-[4,5-b]-pyridin-2-yl | 2-quinolyl | 1750 | 185–190 |
| LII | 0 | 1H-thieno-[3,4-d]-imidazol-2-yl | 2-(N,N-Me)anilyl | 1767 | 137–143 |

Some of the most representative compounds of the invention have been subjected to a pharmaco-toxicological study as hreinafter reported, using as reference compounds cimetidine and omeprazole, parent compound of the new antisecretory compounds class of the proton pump inhibitors.

Toxicity after single administration.

The tests have been carried out in IVA:NMRI (SPF) mice fasted with water ad libitum since 18 hours before treatment.

The compounds were administered by the oral route, at constant volume (10 ml/kg) in a 0.2% aqueous solution of Tween 80.

On the basis of lethality observed 7 days after the treatment, the approximate LD₅₀ were determined according to the Probits method.

| Compound | Code (CHF) | Acute Toxicity (DL₅₀ approx. mg/kg p.o.) |
|---|---|---|
| X | 1376 | 1400 |
| XI | 1472 | 450 |
| XIX | 1477 | 1000 |
| XXI | 1454 | 900 |
| XXII | 1446 | 1000 |
| XXIV | 1450 | 2000 |
| XXIX | 1740 | >>2000 |
| LI | 1750 | 750 |
| Omeprazole HCL | | 1400 |

Antisecretory activity—Shay ulcers

The gastric secretory inhibitory activity of the compounds of general formula (I) was determined in case of hypersecretion induced in the rat by ligation of gastroduodenal junction according to the procedure described by Shay (Shay H. et al, Gasgroenterology 5, 43–61, 1945).

Male CD (Charles River) rats, of body weight higher than 180 g, were fed with a standard diet and housed under constant temperature and relative humidity conditions at least for 5 days before the test. Thereafter, they were fasted for 24 hours, with water ad libitum, which period was sufficient to assure a good gastric emptying, then laparectomized under light ether anesthesia, so as to allow to effect a pylorus ligation as closer as possible to the gastroduodenal junction. Two hours after the ligation, the animals were killed by means of an ether excess and stomachs were removed. Gastric contents were recovered, after filtration through a gauze, and placed in graduated test-tubes and centrifuged at 3000×g for 15 minutes. The following parameters were evaluated on the surnatant: volume (ml); pH; free acidity by conversion of pH into H⁺ µEq by means of Moore table (Ann. New York Acad. Sci. 1967, 866–874); titrable acidity, by titration of an amount with 0.02N NaOH, using phenolphtalein as the indicator.

Both free and titrable acid concentrations were then multiplied by the respective secretion volume, to obtain hydrochloric acid output secreted during the 2 hours ligation.

Compounds under test were administered either by the intraduodenal route, suspended in 0.5% Methocel in a 5 ml/kg volume, immediately after pylorus ligation, or by the intravenous route (1 ml/kg) dissolved in 0.5M methanesulfonic acid, at the moment in which ligation was performed. Control animals were administered with the only solvent, in an amount of 5 ml/kg and 1 ml/kg respectively by the intraduodenal or intravenous routes.

The results were expressed as percent inhibition of hypersecretion induced by pylorus ligation in the control rats.

The obtained results are reported in table 3 as:

$ED_{50}$ (μmol/kg) calculated on the basis of the equation of the linear tract of does-effect curves obtained with the test compounds on volume, free and titrable acidities;

approximate value of intrinsic activity ($\alpha$) where $\alpha = 1$ represents 100% inhibition of gastric acid hypersecretion; and potency ratio (PR) in comparison with Omeprazole (control compound), calculated as ratio of mean $ED_{50}$, on the 3 parameters of the test compound, to mean $ED_{50}$ of the control compound.

minutes intervals by titration of the perfusate with 0.01N NaOH to pH 7.0 using an autotitrator (Radiometer).

After equilibration of basal secretion an hypersecretion was induced by infusion of histamine 35 mcg/kg/min, through the femoral vein.

After reaching of the plateau of the hypersecretive response (60–70' later) the test substances were administered into the duodenum suspended in Methocel in a volume of 5 ml/kg.

Mean gastric output was determined for a 3 hours test period following drug administration. The last 30 minutes interval prior to dosing was used as a control.

The dose-response relationship was established using the maximum inhibition obtained at each individual dose.

$ED_{50}$, intrinsic activity ($\alpha$) and potency rato (PR) are reported in Table 4 except that $ED_{50}$ is not reported for volume since this parameter does not change during lumen perfusion.

TABLE 3

Inhibitory effect of compounds of general formula (I) for the secretion of hydrochloric acid in the stomach (Shay ulcers) in comparison with omeprazole and cimetidine.

| Compounds | $ED_{50}$ (μmol/kg) volume | free acid output | titratable acid output | $\alpha$ | PR |
|---|---|---|---|---|---|
| Omeprazole | 4,2 | 1,8 | 2,3 | 1 | 1 |
| Cimetidine | 47,3 | 24,1 | 23,9 | 1 | 11,5 |
| VIII CHF 1340 | 0,12[1] | 0,03[1] | 0,03[1] | 0,4–0,6 | 0,02 |
| IX CHF 1316 | 65,0 | 53,2 | 24,7 | 0,4–0,6 | 17,2 |
| X CHF 1376 | 10,0 | 2,7 | 2,7 | 0,7–0,8 | 1,9 |
| XI CHF 1472 | 40,0 | 31,9 | 29,6 | 1 | 12,2 |
| XII CHF 1240 | 43,5 | 34,7 | 38,1 | 1 | 14,0 |
| XIV CHF 1338 | 26,7 | 17,1 | 19,2 | 0,6 | 7,6 |
| XV CHF 1360 | 3,0 | 0,6 | 0,7 | 0,5–0,6 | 0.5 |
| XVI CHF 1375 | 2,3 | 0,3 | 0,3 | 0,4–0,6 | 0.3 |
| XVII CHF 1337 | 134,3 | 84,4 | 108,6 | 0,7–0,9 | 39,7 |
| XVIII CHF 1263 | 40,3 | 36,9 | 39,4 | 1 | 14,0 |
| XIX CHF 1477 | 107,8 | 47,3 | 64,3 | 1 | 26,4 |
| XX CHF 1451 | 80,0 | 65,0 | 65,0 | 0,7–0,8 | 25,3 |
| XXI CHF 1454 | 38,0 | 27,0 | 29,0 | 1 | 11,3 |
| XXII CHF 1446 | 30,5 | 16,8 | 22,3 | 0,8 | 8,4 |
| XXIII CHF 1449 | 125,0 | 125,0 | 110,0 | 0,7 | 43,4 |
| XXIV CHF 1450 | 20,5 | 12.5 | 15,7 | 0,7–0,8 | 5,9 |
| XXVIII CHF 1700 | 55,4 | 40,6 | 44,9 | 1 | 17,0 |
| XXIX CHF 1740 | 144,2 | 86,1 | 107,4 | 1 | 40,7 |
| XXX CHF 1757 | 21,1 | 9,2 | 11,2 | 1 | 5,0 |
| XXXI CHF 1759 | 67,2 | 30.1 | 55,1 | 0,9 | 18,4 |
| XXXII CHF 1760 | 34,2 | 25,5 | 23,9 | 1 | 10,1 |
| XXXIII CHF 1765 | 3,0 | 1,2 | 2,0 | 0,7–0,8 | 0,75 |
| XXXIV CHF 1766 | 24,6 | 6,1 | 1,3 | 1 | 3,9 |
| XXXV CHF 1768 | 24,9 | 8,3 | 5,0 | 1 | 4,6 |
| XXXVI CHF 1769 | 120,0 | 50,0 | 80,0 | 0,6–0,7 | 30,1 |
| XXXVII CHF 1458 | 80,0 | 73,0 | 80,0 | 0,6–0,8 | 28,1 |
| XXXIX CHF 1724 | 300,0 | 139,0 | 164,9 | 0,8 | 72,8 |
| XLI CHF 1764 | 124,5 | 42,3 | 61,9 | 1 | 27,6 |
| XLIII CHF 1272 | 89,0 | 83,0 | 81,6 | 1 | 30,6 |
| XLV CHF 1758 | 31,2 | 17,8 | 19,3 | 1 | 8,2 |
| XLVI CHF 1728 | 52,0 | 33,1 | 45,8 | 1 | 15,8 |
| XLVII CHF 1763 | 130,0 | 42,3 | 61,9 | 0,7–0,9 | 28,2 |
| XLVIII CHF 1341 | 521,8 | 164,1 | 234,9 | 0,5–0,6 | 110,9 |
| L CHF 1754 | 19,7 | 5,5 | 6,9 | 1 | 3,8 |
| LI CHF 1750 | 10,3 | 4,8 | 5,6 | 1 | 2,5 |
| LII CHF 1767 | 90,0 | 45,0 | 28,0 | 0,5–0,8 | 19,6 |

[1]$ED_{40}$ value

Lumen-perfused rat stomach in situ

The experiments were done according to Ghosh M. N. and Schild H. O. (Br. J. Pharmacol. 13, 54–61, 1958).

Charles River, CD male rats having a body weight of 280–320 g, deprived of food with free access to water for 24 hours prior to the experiment, were anesthetized with urethane 25% (1.25 g/kg/5 ml i.m.) and tracheotomized. After a midline abdominal incision, a PVC tube was inserted into the stomach via the esophagus and the stomach was perfused with saline (37° C.) at a rate of 1 ml/min. A second tube draining the pylorus was inserted through the abdominal wall for collection of gastric secretion. Acid secretion was determined at 10

TABLE 4

Inhibitory effect of compounds of general formula (I) for the secretion of hydrochloric acid in the stomach in comparison with omeprazole and cimetidine.

| Compounds | ED$_{50}$ ($\mu$mol/kg) free acid output | titratable acid output | $\alpha$ | PR |
|---|---|---|---|---|
| OMEPRAZOLE | 2.23 | 2.30 | 1 | 1 |
| CIMETIDINE | 11.85 | 11.09 | 1 | 5.1 |
| XI CHF 1472 | 60.65 | 40.86 | 1 | 22.4 |
| XXVIII CHF 1700 | 31.39 | 19.89 | 1 | 11.3 |
| XIX CHF 1477 | 32.16 | 26.73 | 1 | 13.0 |

PR = potency ratio

Protection against gastric lesions induced in rats by necrotizing agents

The experiments were done on male rats weighing 260–300 g starved (with free access to water) for 18 hours.

Absolute ethanol was administered by gavage in the volume of 1 ml.

Test substances or the vehicle alone for the controls were given by gavage 30 minutes before the necrotizing agent in a 5% suspension of methylcellulose volume 2.5 ml kg$^{-1}$. One hour after administration of the necrotizing agent, the animals were killed and examined for lesions of the glandular portion of the gastric mucosa. The lesions presenting as blackish lesions grouped in patches of varying size, usually parallel to the major axis of the stomach, were scored according to the following arbitrary scale:

0 = normal mucosa;
1 = hyperemic mucosa, or up to 3 small patches;
2 = from 4 to 10 small patches;
3 = more than 10 small or up to 3 medium-sized patches;
4 = from 4 to 6 medium-sized patches;
5 = more than 6 medium-sized or up to 3 large patches;
6 = from 4 to 6 large patches;
7 = from 7 to 10 large patches;
8 = more than 10 large patches or extensive necrotic zones.

"Small" 0 was defined as up to 2 mm across (max diameter), "medium-sized" as between 2 and 4 mm across and "large" as more than 4 mm across.

Animals with gastric lesion score $\leq 2$ were considered protected.

ED$_{50}$ values were calculated according to Wilcoxon method.

The results are expressed in table 5.

TABLE 5

Protection against gastric hemorrhagic lesions induced by absolute ethanol.

| Compounds | ED$_{50}$ (mg/kg) |
|---|---|
| OMEPRAZOLE | 73 |
| XI CHF 1472 | 20 |
| XIX CHF 1477 | 70 |
| XX CHF 1451 | 50 |
| XXI CHF 1454 | 70 |
| XXII CHF 1446 | 63 |
| XXIV CHF 1450 | 47 |
| XLIII CHF 1272 | 60 |
| LI CHF 1750 | 20 |

A further object of the present invention is provided by the use of compounds of general formula (I) in therapy, in the prophylaxis or inhibition of gastric acid secretion.

Compounds of general formula (I) or the pharmaceutically acceptable salts thereof can be used in the treatment of gastrointestinal diseases associated with acid hypersecretion, such as duodenal ulcer, gastric ulcer, peptic ulcer, esophagitis, Zollinger-Ellison syndrome, bleeding due to ulcer or to erosions of mucosa in gastrointestinal superior tract, relapsing ulcers, postoperatory ulcers.

Moreover, said compounds can be used for the treatment of all those conditions in which a reduction in stomach acid secretion and/or a cytoprotective action are required, such as hypersecretory gastritis and duodenitis, gastritis or dyspepsias associated with the administration of non-steroidal antiinflammatory drugs, in the prophylaxis of gastrointestinal bleedings in stress ulcers and similar conditions.

For therapeutical applications, the compounds of general formula (I) can be formulated in usual pharmaceutical compositions, which provide another object of the invention.

Pharmaceutical compositions containing as the active ingredient one compound of the invention, possibly in combination with pharmaceutically acceptable excipients, can be administered by oral, rectal, parenteral, transdermic, inhalatory or buccal routes, in any administration form.

The amount of the active ingredient is generally 0.1 to 95% by weight on the composition; in solid preparations it is generally 1 to 50% by weight of the composition; in liquid preparations 0.2 to 20% by weight and in parenteral preparations 0.1 to 10% by weight.

Solid compositions for oral administration can be in form of powder, granulates, tablets, capsules or similar forms. In said compositions the active ingredient can be in combination with a powdered solid diluent, such as calcium phosphate, lactose, saccharose, sorbitol, mannitol; potato, cereal or mais starches, dextrine, amylopectin, a cellulose derivative or gelatin, and can also contain a lubricant, such as talcum, magnesium or calcium stearate, polyethylene glycol or silica. Tablets can variously be coated according to well known methods. Hard-gelatin capsules can contain granulates of the active ingredient, together with solid powdered excipients such as lactose, saccharose, sorbitol, mannitol, starches (of the above mentioned type), cellulose derivatives or gelatin, and can also contain stearic acid or magnesium stearate or talc. Soft gelatin capsules can contain the active ingredient in admixture with an appropriate carrier, such as a vegetal oil, PEG, tensides.

Powders and granules can be microincapsulated to obtain a sustained release of the active ingredient. Tablets can be coated by a gastro-resistant coating such as wax, anionic polymers such as cellulose acetate phthalate, hydroxypropylmethylcellulose, partially methyl esterified polymers of methacrylic acid and the like, optionally in combination with a plasticizer. Such a type of formulation is particularly suited for compounds of general formula (I) in which n=1, since said compounds can undergo degradation in acidic medium.

Other stabilization techniques known to those skilled in the art can be applied to the pharmaceutical compounds of the invention: among these, for example, complexation with cyclodextrines.

Liquid compositions for oral administration comprise solutions, suspensions or emulsions of the active ingredient, or of pharmaceutically acceptable salts thereof, in liquid diluents such as distilled water, ethanol, glycerol, non aqueous solvents such as propylene glycol or mixtures thereof.

Injectable formulations for parenteral administration can contain as excipients a pharmaceutically acceptable sterile liquid such as water or a polyvinylpyrrolidone aqueous solution, as well as an oil, such as peanut oil and possibly a stabilizer and/or a buffer. The active ingredient can be dissolved or suspended in the liquid and suitably sterilized or it can be lyophilized, in which case vials containing sterile liquid for injections to prepare the solution before use will be added to the package.

Compositions for rectal administration can be in form of suppositories in which the active ingredient is amixed with a neutral fatty base or with other binding agents or lubricants, such as polymer glycols, gelatins or others, or they can be in form of rectal gelatin capsules, in which the active ingredient is mixed with an appropriate carrier. Other formulations for rectal administration are micro enemas ready to use or to restore at the moment of use.

Topical formulations can be of the conventional type, such as ointments, creams, gels, in form of transdermic systems consisting of adhesive matrices which can be applied to cutis, containing appropriate concentrations of the active ingredient which is gradually released through cutis thus entering hematic circulation.

Inhalatory compositions can be solutions, suspensions, emulsions or powders of the active ingredient to be administered through an aerosol, or to be conditioned in aerosol bombs, using a conventional propeller such as dichlorodifluoromethane, trichlorofluoromethane, dichlorotetrafluoroethane or others.

The present invention also provides sustained released compositions prepared according to conventional techniques.

The daily dosage in man of an active ingredient selected from one of the compounds of general formula (I) can range from 1 to 500 mg, preferably from 10 to 300 mg, depending on the type of treatment as well as on the used composition.

The compounds of the invention can also be combined with other medicaments, such as antacid, non-steroidal antiinflammatories and other antiulcer and/or cytoprotective drugs, such as anticholinergics, antihystaminic anti H$_2$ and prostaglandins.

We claim:

1. A compound of the formula

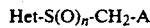

in which Het has the formula

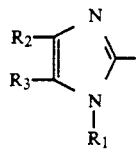

wherein R$_1$ is H, C$_1$–C$_4$ alkyl, benzyl or phenyl which can be substitued by C$_1$–C$_4$ alkyl, C$_1$–C$_4$ alkoxy, trifluoromethyl or halogen at any postion; R$_2$ and R$_3$ are H or phenyl, provided that when R$_1$ is H, R$_2$ and R$_3$ are both phenyl;

A has the formula

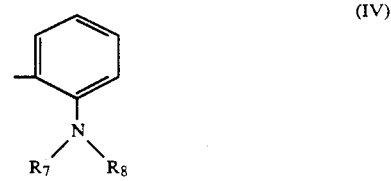

(IV)

wherein R$_7$ and R$_8$, which may be the same or differenct, are H, hydroxyalkyl, C$_1$–C$_4$ alkyl which may be interrupted by the heteroatoms O or N, or together with the N atom to which they are bonded, form a pyrrolidine, piperidine, piperazine or morpholine ring; and n is 0 or 1.

2. A compound according to claim 1, in which Het is 1-methyl-imidazol-2-yl, n is 0 or 1 and A is 2-(N,N-dimethyl)anilyl.

3. A compound according to claim 1, in which Het is 1-phenyl-imidazol-2-yl, n is 0 or 1 and A is 2-(N,N-dimethyl)anilyl.

4. A compound according to claim 1, in which Het is 1-(3-fluorophenyl)imidazol-2-yl, n is 0 or 1 and A is 2-(N,N-dimethyl)anilyl.

5. A compound according to claim 1, in which Het is 1-(4-fluorophenyl)imidazol-2-yl, n is 0 or 1 and A is 2-(N,N-dimethyl)anilyl.

6. A compound according to claim 1, in which Het is 1-(2-chlorophenyl)-imidazol-2-yl, 1-(4-chlorophenyl)imidazol-2-yl, 1-(2-fluorophenyl)imidazol-2-yl, 1-(2-methoxyphenyl)imidazol-2-yl, 1-(4-methoxyphenyl)imidazol-2-yl, 1-(2-trifluoromethylphenyl)imidazol-2-yl, n is 0 or 1 and A is 2-(N,N-dimethyl)anilyl.

7. A compound according to claim 1, in which Het is 4,5-diphenyl-imidazol-2-yl, n is 0 or 1 and A is 2-(N,N-dimethyl)anilyl.

8. A pharmaceutical composition having gastric acid antisecretory activity which comprises as the principal active ingredient an effective amount of a compound according to claim 1 in combination with a pharmaceutically acceptable carrier.

9. A method of therapeutically treating a subject suffering from gastric acidity which comprises administering to said subject an effective amount of a composition according to claim 8.

* * * * *

UNITED STATES PATENT AND TRADEMARK OFFICE
CERTIFICATE OF CORRECTION

PATENT NO. : 5,066,652
DATED : Nov. 19, 1991
INVENTOR(S) : Paolo Chiesi; Vittorino Servadio; Roberta Razzetti It is certified that error appears in the above-identified patent and that said Letters Patent is hereby corrected as shown below:

On the Title page, Item 54, line 3, "Antisectetory" should read ---Antisecretory---

Signed and Sealed this

Twenty-seventh Day of April, 1993

*Attest:*

MICHAEL K. KIRK

*Attesting Officer*      *Acting Commissioner of Patents and Trademarks*